US005731186A

United States Patent [19]
McCaman et al.

[11] Patent Number: 5,731,186
[45] Date of Patent: Mar. 24, 1998

[54] METHOD FOR THE PRODUCTION OF RDSPA α1

[75] Inventors: Michael McCaman, San Bruno; Erno Pungor, Millbrae; Carol Souders, Los Altos; Mei P. Tan, San Mateo, all of Calif.

[73] Assignee: Schering Aktiengesellschaft, Berlin, Germany

[21] Appl. No.: 597,059

[22] Filed: Feb. 5, 1996

[51] Int. Cl.$^6$ .............................. C12N 9/48; C12N 9/50; C12N 9/68; C12P 21/06
[52] U.S. Cl. ..................... 435/212; 435/69.1; 435/94; 435/215; 435/216; 435/226; 530/380
[58] Field of Search ................... 435/69.1, 94.3, 435/212, 215, 216, 226; 530/380, 395

[56] References Cited

U.S. PATENT DOCUMENTS

| | | |
|---|---|---|
| 4,721,572 | 1/1988 | Jordan . |
| 4,898,825 | 2/1990 | Morii et al. . |
| 4,929,560 | 5/1990 | Edmunds et al. . |
| 4,978,620 | 12/1990 | Morii et al. . |
| 5,015,583 | 5/1991 | Pâques . |
| 5,141,862 | 8/1992 | Patel et al. . |

FOREIGN PATENT DOCUMENTS

| | | |
|---|---|---|
| 0 352 119 A2 | 7/1989 | European Pat. Off. . |
| 0 383 417 A1 | 2/1990 | European Pat. Off. . |
| 0 436 261 A1 | 12/1990 | European Pat. Off. . |

OTHER PUBLICATIONS

Kratzschmar et al Jan. 1, 1992 Gene 116 p. 281.
Witt et al. Jul. 1, 1994 Circulation 90 (1) p. 421.
Bringmann et al., "Structural Features Mediating Fibrin Selectivity of Vampire Bat Plasminogen Activators", *J. Biol. Chem.*, (1995) 270:25596–25603.
Petri et al., "Production of vampire bat plasminogen activator DSPA α1 in CHO and insect cells", *J. Biotech.*, (1995) 39:75–83.
Witt et al., "Thrombolytic Properties of *Desmodus rotundus* (vampire bat) Salivary Plasminogen Activator in Experimental Pulmonary Embolism in Rats", *Blood*, (1992) 79(5):1213–1217.
Krätzschmar et al. "The plasminogen activator family from the salivary gland of the vampire bat *Desmodus rotundus*: cloning and expression", *Gene*, (1991) 105:229–237.
Gardell et al., "Isolation, Characterization and cDNA Cloning of a Vampire Bat Salivary Plasminogen Activator", *J. Biol. Chem.*, (1989) 264(30):17947–17952.

*Primary Examiner*—Marian C. Knode
*Assistant Examiner*—Mary K. Zeman
*Attorney, Agent, or Firm*—Wendy L. Washtien

[57] ABSTRACT rDSPA α1 is produced in commercial quantities and a purity adequate for clinical standards. The production methods utilize a series of chromatographic steps: cation exchange chromatography, followed by hydrophobic interaction chromatography, and ending with affinity chromatography.

23 Claims, No Drawings

METHOD FOR THE PRODUCTION OF RDSPA α1

FIELD OF THE INVENTION

The present invention is directed to a method for the isolation and purification of recombinant *Desmondus rotundus* salivary plasminogen activator α1 (rDSPA α1), to rDSPA α1 purified by this process, to pharmaceutical compositions containing rDSPA α1 so purified, and to methods for treatment using rDSPA α1 so purified.

BACKGROUND OF THE INVENTION

Thromboses are produced by the formation of a blood clot in blood vessels. One distinguishes between venous thromboses including pulmonary embolisms and arterial thromboses including acute myocardial infarction. Pulmonary embolism and cardiac infarction are life-threatening events requiring immediate medical intervention.

A popular form of therapy for such arterial and venous thromboses is the use of plasminogen activators to perform enzymatic thrombolysis (Collen et at., *Ann. Rev. Med.*, (1988), 39: 405-423). These substances, called thrombolytics, convert plasminogen, the inactive proenzyme of the fibrinolysis system in the blood, into the active proteolytic enzyme, plasmin. Plasmin, in turn, dissolves the fibrous substance fibrin, which is a substantial component of a blood clot; this leads to reopening of the blocked vessels and restoration of blood flow. However, because plasmin is a relatively nonspecific protease, it can also destroy, through proteolysis, components in the blood indispensable for intact hemostasis (e.g. fibrinogen) and thus increase the risks of hemorrhaging.

The first enzymatic thrombolytics, streptokinase and urokinase, are compounds which, once injected into the circulation, systemically convert plasminogen into plasmin and induce systemic proteolysis. Thus, thrombolysis therapies which use these compounds are accompanied by the complications related to hemorrhage. Newer thrombolytic therapies, based on the use of plasminogen activators of the tissue type, commonly referred to as t-PA, have been developed but they are also beset by a number of drawbacks, including serious bleeding complications, a relatively frequent incidence of reocclusion, an inability to be uniformly effective, and susceptibility to inactivation by plasminogen activator inhibitors such as Type 1 plasminogen activator inhibitor (PAI-1) (Loskutoff, *Seminars in Thrombosis and Hemostasis*, Vol. 14, No. 1 (1988)).

More recently, plasminogen activator proteins have been purified from vampire bat (*Desmondus rotundus*) saliva and salivary glands (European Published Patent Application 0 383 417 (Baldus et al.); European Published Patent Application 0 352 119 (Duong et al.)). These plasminogen activators (referred to as DSPA) are serine proteases which catalyze the conversion of plasminogen to plasmin but they exhibit greater selectivity towards fibrin-bound plasminogen and, hence, may be associated with decreased severity and frequency of bleeding when used for thrombolytic therapy. Furthermore, DSPA is not readily inactivated by plasma inhibitors such as PAI-1, and therefore, may be associated with a lower frequency of reocclusion.

Two high molecular weight forms of DSPA (designated α1 and α2) can be found in bat saliva, both of which consist of several domains, including a protease domain, and both of which are capable of tightly binding to plasminogen in the presence of fibrin. The various forms of DSPA have been produced in mammalian cell culture by recombinant biotechnology (Krätzschmer et al., *Gene* (1991), 105: 229-237; European Published Patent Application 0 352 119 (Duong et al.)) and small scale purification of recombinantly produced DSPA (rDSPA) has been described (Witt et al., *Blood* (1992), 79: 1213–1217). However, the isolation and purification of rDSPA on a commercial scale and in a state of purity suitable for pharmaceutical formulations has not been disclosed.

The instant application is concerned with isolation and purification of recombinant DSPA α1 (rDSPA α1) on a commercial scale. The invention as described results in rDSPA α1 sufficiently pure and stable to be sold commercially and to be clinically usable.

SUMMARY OF THE INVENTION

The present invention provides a method for the isolation and purification of rDSPA α1 on a commercial scale, and results in product which is suitable for clinical use.

Accordingly, an aspect of the invention is directed to a method for purifying rDSPA α1 from a biological medium, said method comprising the following steps:

(a) applying the medium to a cation exchange resin under loading conditions which result in selective binding of rDSPA α1 to the cation exchange resin;

(b) optionally, washing the cation exchange resin to remove non-rDSPA α1 proteins and non-protein contaminants;

(c) selectively eluting the bound rDSPA α1 from the cation exchange resin;

(d) applying the rDSPA α1 -containing eluent from step (c) to a hydrophobic interaction resin under loading conditions which result in selective binding of rDSPA α1 to the hydrophobic interaction resin;

(e) optionally, washing the hydrophobic interaction resin to remove non-rDSPA α1 protein and non-protein contaminants;

(f) selectively eluting the bound rDSPA α1 from the hydrophobic interaction resin;

(g) applying the rDSPA α1-containing eluent from step (f) to an affinity chromatography resin under loading conditions which result in the selective binding of rDSPA α1 to the affinity chromatography resin;

(h) optionally, washing the affinity chromatography resin to remove non-DSPA α1 protein and non-protein contaminants;

(i) selectively eluting the bound rDSPA α1 from the affinity chromatography resin to produce substantially pure rDSPA α1 in an aqueous solution.

Another aspect of the invention is rDSPA α1 protein which has been isolated and purified by the method of the instant application.

Another aspect of the invention is directed toward a pharmaceutical composition containing rDSPA α1 which has been isolated and purified by the method of the instant application, and a pharmaceutically acceptable excipient.

Another aspect of the invention is a method of using rDSPA α1 isolated and purified by the method of the instant application to treat a human with arterial or venous thromboses.

DETAILED DESCRIPTION OF THE INVENTION

As used in the specification and appended claims, unless specified to the contrary, the following terms have the meaning indicated:

"Biological medium" refers to a precise recipe of salts and nutrients used to propagate cells in culture.

"Conditioned medium" refers to a biological medium in which cells have been grown. The medium has, therefore, been conditioned by the growth of the cells and contains products excreted into the medium during cell growth. These can be both waste products produced during growth or proteins which have been made and secreted into the medium by the cells during growth.

"Cation exchange resin" refers to a natural or artificial substance, usually a solid, which is able to exchange bound ions for ions from the surrounding liquid medium. A cation exchange resin has negative functional fixed ions and exchanges positive counter-ions. The anchor groups (exchange-active components) in commercially available cation exchangers are usually —$C_6H_5O^-$, —$SO_3^-$, —$COO^-$, —$PO_3^{--}$, or —$AsO_3^{--}$. Weaker cation exchange resins are those in which the binding strength of the cation is not high, such as those with carboxyl or carboxyalkyl functionalities. Furthermore, weaker cation exchange resins are usually not fully dissociated at acidic pH. A particular weak cation exchange resin used in the invention is comprised of a matrix of silica particles covalently bound to polyethyleneimine silane, wherein the amino groups of the polyethyleneimine have been derivatized with carboxyl groups. Such a resin is commercially available from J. T. Baker, under the trade name Widepore CBX® chromatography resin.

"Hydrophobic interaction resin" refers to a natural or artificial substance, usually a solid, which contains uncharged groups, such as methyl, ethyl, or other alkyl groups. These groups form hydrophobic bonds with groups on protein moieties which are passed through the resin and result in separation of proteins based on the strength of interaction between the protein and resin groups. A particular hydrophobic interaction resin is composed of semi-rigid spherical beads synthesized by a copolymerization of ethylene glycol and methacrylate type polymers derivatized with butyl groups. Such a resin is commercially available from Toso-Haas, under the trade name Toyo-Pearl® 650M C4.

"Affinity chromatography resin" refers to a natural or artificial substance, usually a solid, which is used for the purification of proteins. The resin separates proteins based on the affinity which occurs between groups on the protein and groups on the resin. In the instant invention, the resin used as an affinity chromatography resin is usually used as a size exclusion resin to separate proteins based on their size. A particular affinity chromatography resin is a cross-linked co-polymer of allyl dextran and N,N'-methylene bisacrylamide in the form of beads which are capable of fractionating globular proteins between 20,000 and 8,000,000 kDa. Such a resin is commercially available from Pharmacia, under the trade name of Sephacryl® S-400.

"Alkyl" refers to a straight or branched chain monovalent radical consisting solely of carbon and hydrogen, containing no unsaturation and having from one to eighteen carbon atoms, preferably from one to six carbon atoms, e.g. methyl, ethyl, n-propyl, isopropyl (1-methylethyl), n-butyl, t-butyl (1,1-dimethylethyl), sec-butyl (1-methylpropyl), n-pentyl, n-hexyl, and the like.

"Substantially pure" as applied to the purity of the rDSPA α1 product following the purification scheme detailed in this application means that greater than 80% of the total protein in the final purification product is rDSPA α1, preferably greater than 90% of the total protein isolated is rDSPA α1 and most preferably 98% of the total protein isolated is rDSPA α1. Protein content and purity are based on reverse phase HPLC and SDS-page gel analysis.

"Non-rDSPA α1 protein and non-protein contaminants" refers to all material other than rDPSA α1 found within the biological media from which rDSPA α1 is being purified.

"Pharmaceutically acceptable excipient" refers to an acceptable carrier, and any pharmaceutically acceptable auxiliary substance as required to be compatible with physiological conditions, which are non-toxic and do not adversely effect the biological activity of the pharmaceutical composition suspended or included within it. Suitable excipients would be compounds such as mannitol, succinate, glycine, or serum albumin.

"Therapeutically effective amount" refers to that amount of rDSPA α1 which, when administered to a human in need thereof, is sufficient to effect treatment, as defined below, for disease-states characterized by thrombosis. The amount of a compound which constitutes a "therapeutically effective amount" will vary depending on the compound, the disease-state and its severity, but can be determined routinely by one of ordinary skill in the art having regard to his own knowledge and to this disclosure.

"Treating" or "treatment" as used herein cover the treatment of a disease-state in a human, which disease-state is characterized by thrombosis, and include:

(i) preventing the disease-state from occurring in a human, in particular when such human is predisposed to the disease-state but has not yet been diagnosed as having it;

(ii) inhibiting the disease-state, i.e., arresting its development; or (iii) relieving the disease-state, i.e., causing regression of the disease-state.

"Optional" or "optionally" means that the subsequently described event of circumstances may or may not occur, and that the description includes instances where said event or circumstance occurs and instances in which it does not.

DESCRIPTION OF THE PREFERRED EMBODIMENTS

The present invention is directed to a method for the isolation and purification of rDSPA α1 on a commercial scale and in a form suitable for use in pharmaceutical formulations. The rDSPA α1 is produced by fermenting a mammalian cell line capable of secreting the rDSPA α1 product into the culture media. The conditioned media, i.e. that media obtained from the bioreactor containing the mammalian cells, is harvested, and the rDSPA α1 is separated from other proteins and contaminants by a series of chromatographic steps, beginning with the use of a cation exchange resin, followed by selective elution of the rDSPA α1 from the resin. The rDSPA α1 fraction obtained by selective elution from the cationic exchange resin is then applied to a hydrophobic interaction resin, where a selective elution from the matrix provides a second level of purification. The eluted rDSPA α1 fraction is then applied to an affinity chromatography resin, where selective elution provides a further level of purification. The purified rDSPA α1 is next concentrated by conventional techniques, such as ultrafiltration, and then lyophilized.

Specifically, the invention is practiced as described below.

A. Isolation and Purification

1. Culture Media and Cell Lines

The culture medium comprises a base medium suitable for mammalian cell growth, such as DMEM or Ham's F12.

A particular medium is William's E medium (Williams, G. M. and Gunn, J. M, *Exp. Cell Res.*, (1974) 89:139). For the inoculation growth phase, the base medium will usually be supplemented with a serum source, typically bovine serum (BS) or newborn calf serum (CS), present at a concentration in the range from about 0.1% to 10% by weight, usually being present at about 1% to 5% by weight. Other growth factors or buffers, such as HEPES, may also be added. During the perfusion growth phase, the serum concentration is usually maintained at the same concentration, typically being in the range from about 3% to 8%, usually being about 5%.

Cell lines suitable for use in the present invention include mammalian cell lines capable of non-adherent growth in suspension culture and/or adherent growth on microcarrier beads. Particular cell lines which meet these requirements include Chinese hampster ovary (CHO) cell lines, BHK cells, or the HEK293 cell line (Kraatzschmer et al., *Gene*, (1991) 116: 281–284; Petri, T., *J. BioTechnology*, (1995) 39: 75–83).

A particularly preferred CHO cell line is DXB11, which is described in Urlaub, G. and Chasin, L. A., *Proc. Natl. Acad. Sci. USA*, (1980) 77: 4216–4220. These cells have been co-transfected with the expression vectors pSVPA11 and pUDHFR1, which contain the coding sequences for DSPA α1 and mouse dihydrofolate reductase, respectively (Petri, T., ibid). The transformed CHO cell line used in the present invention is designated CD16 and has been deposited with the American Type Culture Collection, Rockville, Md. (ATCC) and have been given ATCC #CRL-12023.

2. Expansion of Culture and Production Phase

After inoculation with either confluent spinner cultures or portions of other bioreactor cultures, the cell culture will be expanded to production density, typically in the range from about $1-40 \times 10^6$ cells/ml.

After the desired cell density on microcarrier beads is achieved, perfusion of fresh media supplemented with serum is initiated. Alternatively, cells may be grown in suspension culture. Typically, the concentration of the serum in the fresh media will be in the range from about 2% to 10% by weight, more typically in the range from about 3% to 8% by weight, and more normally being about 5% by weight. Initially, the perfusion rate will be in the range from about 0.25 to 0.75 culture volumes/day, typically being about 0.5 culture volumes/day. As the cell growth increases, the perfusion rate is increased to a final rate in the range from about 1.5 to 2.5 culture volumes/day, typically over a period of about 2 to 10 days. During the expansion, sterile, pre-equilibrated microcarrier beads are added to the reactor to maintain the microcarrier bead to cell density ratio in the range from about 0.5 to 1.0 grams of microcarrier beads to $10^9$ cells. Conveniently, the microcarrier beads are added to the reactor using an aspirator through the sample line.

After cell density has reached the production level, the serum addition to the fresh culture medium will be reduced, typically to a concentration in the range from about 0.1 to 2.0 weight percent, typically 1%.

The culture in production phase requires attention to multiple fermentation parameters: temperature, pH, and the level of dissolved oxygen are monitored daily. Additional culture media, serum, and alkali need to be provided as the supply tanks are depleted. Samples of the conditioned media, defined as media which contains product, are analyzed routinely, at least every two days to assure that production continues free from contamination.

The procedure for collection of the conditioned media from bioreactors minimizes the harvesting of cells by using screens with approximately 100–150 micron pore diameters. Suspension cultures use a vortex flow filter to retain cells in the bioreactor. The harvest is collected in sterile containers and stored for up to 38 days before further processing. rDSPA α1 found in the bioreactor harvest has been secreted from the CHO cells in a processed form which has full biological activity and is ready for purification.

3. Cation Exchange Chromatography

After pH adjustment to the range from 4 to 6, preferably to about 5, the rDSPA α1 in the conditioned media is applied to a cation exchange matrix (usually packed in the form of a column) under conditions selected to provide essentially complete binding of rDSPA α1 to the matrix. While other proteins will also be bound, the initial binding stage provides a first level of separation as a number of the undesired or contaminating proteins and other compounds, such as phenol red, in the conditioned media will be unable to bind to the matrix and thus will flow through the matrix. The rDSPA α1 is further purified by selective elution from the matrix, where the elution may be accomplished by either a stepwise elution or linear gradient elution by increasing the ionic strength of the buffer. In either case, the rDSPA α1 is collected for further purification as described below.

Suitable cation exchange matrices include a wide variety of resins derivatized with cationic functionalities which are able to bind rDSPA α1. Preferred are synthetic resins, such as those comprised of silica gel particles, cross-linked agarose, or cross-linked polymethacrylate polymers, derivatized with cationic functionalities such as carboxyl, carboxymethyl, sulfonyl, phosphoryl, and the like. Particularly useful are relatively weak resins, such as those having carboxyl or carboxyalkyl functionalities, such as carboxymethyl or carboxyethyl. A particularly preferred resin is comprised of a matrix of silica particles covalently bound to polyethyleneimine silane, with amino groups of the polyethyleneimine silane derivatized with carboxyl groups. Such a resin is Baker Widepore CBX® (45 μm bead size), which is commercially available from J. T. Baker.

The binding and elution conditions will vary depending on the binding strength of the cationic resin. For weak cationic resins, such as Baker Widepore CBX, binding may be effected at low ionic strength under slightly acidic conditions, typically pH 4–7, preferably about pH 5. After washing the matrix, the rDSPA α1 may be selectively eluted by exposing the matrix to a mobile phase having an elevated ionic strength, employing either linear or step-wise elution. For the Baker Widepore CBX resin, the rDSPA α1 will elute at a pH of about 7.5, with a salt concentration between about 100 mM and 500 mM NaCl. The column may then be stripped and regenerated for subsequent use.

Preferably, with the Baker Widepore CBX matrix, the resin will initially be equilibrated with a buffer of 100 mM sodium acetate, pH 5. Buffer is applied to the column at a flow rate of 0.2 to 2.0 column volumes per minute until the pH of the effluent stabilizes at 5. The conditioned media containing rDSPA α1 is filtered with a 1.2 um filter and then titrated to a pH between 4 and 7, most preferably 5, using glacial acetic acid. The media is then applied to the column, typically using a gear pump, at a flow rate no greater than 2.0 column volumes per minute. A filter is provided to remove particulates which might plug the column matrix. The column matrix is then re-equilibrated with the acetate equilibration buffer until the pH stabilizes at 5, typically requiring from about 2 to 7 column volumes. A wash buffer containing 50 mM sodium phosphate, pH 7.5 is next applied to the column at about 0.1 to 0.2 column volumes per minute until the pH of the eluent stabilizes at 7.5. rDSPA α1 is then eluted from the column using an elution buffer containing 50 mM sodium phosphate, 500 mM sodium chloride, pH 7.5. The elution buffer is run until no more protein is found eluting from the column. A stripping buffer containing 2.0M sodium acetate, pH 8 is then applied to the column in order to regenerate the matrix. The storage buffer contains 10% acetic acid and 45% ethanol.

4. Hydrophobic Interaction Chromatography

The rDSPA α1 fraction collected from the cation exchange matrix is next applied to a hydrophobic interaction matrix (usually in the form of a column) under conditions which allow binding of the rDSPA α1 to the matrix, typically high ionic strength and low pH. The rDSPA α1 is then selectively eluted by increasing the organic solvent concentration of a mobile phase applied to the column, using a linear or a step-wise gradient. The rDSPA α1 fraction is collected for further purification. This step reduces DNA contamination by 100 to 1000 fold and inactivates potential vital contaminants.

Suitable hydrophobic interaction matrices include a wide variety of uncharged resins having covalently attached hydrophobic groups, such as propyl, butyl, octyl, phenyl, and the like. The resins may be cross-linked organic polymers, such as styrene-divinylbenzene, silica, agarose, polymethacrylate, or any one of a wide variety of other suitable particulate supports. A particularly preferred resin is comprised of semi-rigid spherical beads synthesized by a copolymerization of ethylene glycol and methacrylate type polymers derivatized with butyl groups. Such a resin is Toyo-Pearl® 650M (40–90 um beads) which is commercially available from Toso-Haas.

Binding to the hydrophobic interaction column is effected under conditions of high ionic strength, usually at an acidic pH from 3–5, more usually about 4. Substantially all the protein contained in the rDSPA α1 fraction which had been eluted from the cation exchange resin is bound to the hydrophobic interaction column. The various proteins may be selectively eluted based on the differing strengths of hydrophobic interaction with the hydrophobic groups on the matrix, i.e., in order of increasing hydrophobicity of the protein. Elution may be performed with a step-wise or linear gradient, usually with an alcohol eluant, such as ethanol or isopropanol. A particularly preferred alcohol is ethyl alcohol.

Preferably, with the Toyo-Pearl C4 matrix, equilibration may be performed with an equilibration buffer having 50 mM sodium acetate, 500 mM sodium chloride, pH 4. After the rDSPA α1 fraction from the ion exchange column is titrated to pH 4, it is applied to the C4 matrix, and the matrix is then re-equilibrated with the equilibration buffer described above. The column is then washed sequentially with two buffers, as follows. The first wash (Wash 1) uses at least two column volumes of a buffer containing 20 mM HCl. Washing is continued until the effluent contains no further protein, as evidenced by a steady UV absorbance. The matrix is then washed (Wash 2) with not less than 10 column volumes of a buffer containing 19% ethanol, 20 mM HCl, and washing is continued with a buffer containing 20.5% ethanol, 20 mM HCl until no further protein is eluted. Elution of the rDSPA α1 product is effected using a buffer containing 29% ethanol, 20 mM HCl, pH 2.5. After eluting the product, the column is stripped with not less than two column volumes of a buffer containing 100 mM NaOH. The matrix is stored in Wash 1 buffer.

5. Affinity chromatography

The rDSPA α1 fraction collected from the hydrophobic interaction resin is next applied to an affinity matrix (usually in the form of a column) under conditions which allow binding of the rDSPA α1 to the affinity matrix. While the rDSPA α1 remains bound to the column, contaminants are eluted by washing the column with 2 to 3 column volumes of 20 mM HCl. This step facilitates a buffer exchange to aid pharmaceutical formulation and solubility and also helps in the inactivation/removal of potential viral contaminants. Preferably, 2.5 column volumes of the buffer is used. The rDSPA α1 is then selectively eluted using a buffer containing 200 mM glycine, free base at a pH between 4 and 5. The rDSPA α1 fraction is collected for concentration.

In this invention, the resins used as affinity resins are ones which are normally used as size exclusion resins. Suitable affinity matrices include resins comprised of a cross-linked polymer of allyl dextran and N,N'-methylene bisacrylamide in the form of beads with a diameter between 25 and 75 um. A particularly preferred resin is Sephacryl 400®, which is commercially available from Pharmacia and is capable of fractionating globular proteins between 20,000 and 8,000,000 kDa.

Binding of rDSPA α1 to the affinity resin is achieved under conditions of low ionic strength and low pH. Substantially all the rDSPA α1 collected from the hydrophobic interaction resin is bound to the column. The rDSPA α1 may be selectively eluted by raising the pH and/or ionic strength. Elution may be performed with a step-wise or linear gradient, usually with an eluent containing 200 mM glycine, free base.

Preferably, with the Sephacryl S-400 matrix, equilibration may be performed with a buffer having 19% ethanol, 20 mM HCl, until the pH of the effluent remains unchanged. The matrix is loaded with the rDSPA α1 fraction from the hydrophobic interaction column, and then washed with a buffer containing 20 mM HCl until the UV signal from the effluent is steady. Elution of bound rDSPA α1 is effected using a buffer containing 200 mM glycine. After eluting the product, the column is stripped with not less than two column volumes of a buffer containing 100 mM NaOH. Following washing of the matrix with at least two column volumes of the wash buffer (20 mM HCl), the matrix can be stored in this buffer.

6. Concentration

The purified protein of the present invention may then be concentrated, typically by filtration, or the like, and may eventually be lyophilized or otherwise incorporated into conventional pharmaceutical preparations. Useful concentration and lyophilization methods are well described in the scientific literature.

B. Formulation

1. Pharmaceutical compositions

This invention provides a reagent with significant therapeutic value, rDSPA α1, purified by the methods described, which should be useful in the treatment of arterial and venous thromboses.

Recombinant DSPA α1, purified as described herein, can be administered to a patient. This reagent can be combined for therapeutic use with other ingredients, e.g., in conventional pharmaceutically acceptable carriers or diluents, along with physiologically innocuous stabilizers and excipients. These combinations can be sterile filtered and placed into dosage forms as by lyophilization in dosage vials or storage in stabilized aqueous preparations.

The quantities of reagent necessary for effective therapy will depend upon many different factors, including means of administration, physiological state of the patient, and other medicants administered. Thus, treatment dosages should be titrated to optimize safety and efficacy. Typically, dosages used in vitro may provide useful guidance in the mounts useful for in situ administration of these reagents. Animal testing of effective doses for treatment will provide further predictive indication of human dosage. Various consideration are described, e.g., in Gilman et at. (eds) (1990) *Goodman and Gilman's: The Pharmacological Bases of Therapeutics*, 8th Ed., Pergamon Press; and *Remington's Pharmaceutical Sciences*, 18th ed. (1990), Mack Publishing Co., Easton, Pa.; each of which is hereby incorporated by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the Merck Index, Merck & Co., Rahway, N.J. Based on the dosages required of other plasminogen activators, the need for a total dosage of between 80 and 110 mg would be expected (*Physicians' Desk Reference*, 49th ed.(1995), Medical Economics Data Production Company, pp 1083–1085).

Therapeutic formulations may be administered in any conventional dosage formulation. While it is possible for the active ingredient to be administered alone, it is preferable to present it as a pharmaceutical formulation. Formulations comprise at least one active ingredient, as defined above, together with one or more acceptable carriers thereof. Each carrier must be both pharmaceutically and physiologically acceptable in the sense of being compatible with the other ingredients and not injurious to the patient. Formulation include those suitable for oral or parenteral (including subcutaneous, intramuscular, intravenous and intradermal) administration. The formulations may conveniently be presented in unit dosage form and may be prepared by any methods well known in the art of pharmacy. See, e.g. Gilman et. at., ibid, and Remington ibid.

In summary, the preferred embodiments of the invention as described in the Summary of the Invention are as follows:

a method for the isolation and purification of rDSPA α1 from a biological medium, said method comprising the following steps:

(a) applying the medium at a pH of 5 to a cation exchange resin comprised of a matrix of silica particles covalently bound to polyethyleneimine silane, wherein the amino groups have been derivatized with carboxyl groups, which results in selective binding of rDSPA α1 to the cation exchange resin;

(b) washing the cation exchange resin at pH 5 with 100 mM NaOAc and 50 mM $NaPO_4$ at pH 7.5, to remove non-rDSPA α1 protein and non-protein contaminants;

(c) eluting the bound rDSPA α1 from the cation exchange resin with a buffer containing 50 mM sodium phosphate and 500 mM sodium chloride at pH 7.5;

(d) applying the rDSPA α1-containing eluent from step (c) at pH 4 to a hydrophobic interaction resin comprised of semi-rigid spherical beads synthesized by a copolymerization of ethylene glycol and methacrylate type polymers derivatized with butyl groups, which results in selective binding of rDSPA α1 to the hydrophobic interaction resin;

(e) washing the hydrophobic interaction resin with 20 mM HCl and then with 20 mM HCl containing 19% EtOH to remove non-rDSPA α1 protein and non-protein contaminants;

(f) eluting the bound rDSPA α1 from the hydrophobic interaction resin with a buffer containing 29% ethanol and 20 mM hydrochloric acid at pH 2.5;

(g) applying the rDSPA α1-containing eluent from step (f) at pH 2.5 to an affinity chromatography resin comprised of a cross-linked polymer of allyl dextran and N,N'-methylene bisacrylamide which fractionates globular proteins between 20,000 and 8,000,000 kDa, which results in the selective binding of rDSPA α1 to the affinity chromatography resin;

(h) washing the affinity chromatography resin with 20 mM HCl to remove non-rDSPA α1 protein and non-protein contaminants;

(i) eluting the bound rDSPA α1 from the affinity chromatography resin with a buffer containing 200 mM glycine at a pH between 4 and 5, to produce substantially pure rDSPA α1 in an aqueous solution.

The following specific preparations and examples are provided as a guide to assist in the practice of the invention, and are not intended as a limitation on the scope of the invention.

EXAMPLE 1

Cell Culture Production of rDSPA α1

A vial from the DSPA Working Cell Bank was thawed and inoculated into a roller bottle with 5% calf serum in growth media (WEC 5.0 media, Williams E modified). Over a two week period the cells were expanded into four roller bottles, the cells were trypsinized from the roller bottles and inoculated into four 1 L spinner flasks at $4\times10^8$ cells each in 1 L of growth media. After four days, the cultures from the four spinners were used to inoculate a 10 L bioreactor. An additional 1 L of growth media was added to the bioreactor culture on the day of inoculation. The next day, the bioreactor was filled to 10 L with growth media. Culturing both with and without addition of microcarrier beads followed this protocol. The medium pH was controlled at 7.0–7.4 and oxygenation was maintained at all times by a sparging system. The temperature was maintained at 34°–39° C.

The cell density on the day of inoculation in the bioreactor was $8.1\times10^5$ cells per mL and after two days the cell density had doubled, at which time the perfusion rate was set at 0.5 culture volumes per day (cv/day). The perfusion rate was increased in relation to cell density such that by nine days post inoculation of the bioreactor the density had reached $6.2\times10^6$ cells/mL and perfusion increased to 2 cv/day.

The bioreactor was then switched to production media (1% calf serum in WEC 5.0 media) and two days later collection of production harvest began and continued for as long as 10 weeks. During the production phase, the average cell density was $15\times10^6$ cells per mL with approximately 75% viability. The average rDSPA α1 production was 40 milligrams rDSPA α1 per liter and average specific production rate was 6 picograms rDSPA α1 per cell per day.

Expansion of fermentation volumes was achieved by transferring half the contents of one reactor to a new vessel. Both bioreactors were placed in production media, perfused at 2 cv/day, and collection of production harvest began immediately.

EXAMPLE 2

Purification of rDSPA α1

1. Cation Exchange Chromatography (Column A). The bioreactor harvest is stored at ambient temperature (15°–25° C.). It is then filtered through a 0.45 micron filter prior to loading onto a cation exchange column. Purification of the harvest begins with a column chromatography step using the CBX resin made by J. T. Baker (Column A). This step facilitates a significant purification of the protein.

The Column A buffers consist of Buffer A1: Equilibration buffer (50 mM NaoAc, pH 5.0), Buffer A2: Wash buffer (50 mM NaPO4, pH 7.5), Buffer A3: Elution buffer (50 mM NaPO4, 500 mM NaCl, pH 7.5), Buffer A4: Strip buffer (2 M NaAc, pH 8.0), and Buffer A5: Storage buffer (45% EtOH, 10% HoAc).

The following column operating parameters are appropriate for a column packed with 6 kg of resin and has a column volume of 15 liters. Not more than 4.5 grams of rDSPA α1 can be loaded on the column per ran. The column is loaded at a flow rate of not more than 2 liters per minute and not more than 20 psi column pressure. The column and monitor specifications are checked prior to each run. The load material and chromatographic buffers are degassed by sparging with helium prior to use.

The bioreactor harvest is filtered with a 1.2 μm filter then titrated to pH 5.00 (±0.10) using glacial acetic acid. Prior to loading, the column is equilibrated with not less than 30 liters of Buffer A1 until the effluent is pH 5.00 (±0.20). Once the column is equilibrated, the harvest is loaded on the column. The column is re-equilibrated with not less than 80 liters of Buffer A1. The column is properly re-equilibrated when the effluent is pH 5.00 (±0.20) and when a stable UV baseline is reached. The column is washed with not less than 145 liters of Buffer A2. The column is properly washed when the effluent is pH 7.50 (±0.20) and when a stable UV baseline is reached.

The product is eluted from the column with not less than 30 liters of Buffer A3 and collected in a separate vessel. Elution is considered complete when a stable UV baseline is reached. After eluting the product, the column is stripped until a stable UV baseline is achieved, using not less than 30 liters of Buffer A4. The column is then cleaned for reuse (not to exceed 50 cycles of use). The Column A product (or eluate) is stored at 2°–8° C. The average recovery was 93% and the average (protein) purity of the eluate was 81%.

2. Hydrophobic Interaction Chromatography (Column B). Following chromatography on the CBX resin, the rDSPA α1 product is chromatographed using a C4 hydrophobic interaction resin (Toso-Haas) (Column B). This step facilitates significant removal of non-protein contaminants and also helps in the inactivation/removal of possible viral contaminants. The Column B buffers consist of Buffer B 1: Equilibration buffer (50 mM NaoAc, 500 mM NaCl, pH 4.0), Buffer B2: Wash and Storage buffer (20 mM HCl), Buffer B3: Wash buffer (20 mM HCl,19% EtOH), Buffer B4: Wash buffer (20 mM HCl, 20.5% EtOH), Buffer B5: Elution buffer (20 mM HCl, 29.5% EtOH), and Buffer B6: Strip buffer (0.1N NaOH). The following column operating parameters are appropriate for a column volume of 15 liters. Not more than 9 grams of rDSPA α1 can be loaded on the column per run. The column is loaded at a flow rate of not more than 2 liters per minute and not more than 15 psi column pressure. The column and monitor specifications are checked prior to each run.

Prior to loading, the column is equilibrated until the effluent is pH 4.00 (±0.20). The Column A eluate is titrated to pH 4.00 (±0.10) using glacial acetic acid, degassed, and loaded. This column is re-equilibrated with not less than 30 liters of Buffer B1 until the effluent is pH 4.00 (±0.20) and a stable UV baseline is reached. The column is washed with three buffers. The first wash is with not less than 45 liters of Buffer B2. The column is properly washed when the effluent is pH 1.90 (±0.20) and when a stable UV baseline is reached.

The column is washed a second time with not less than 145 liters of Buffer B3 until a stable UV baseline is reached. The column is washed a third time with not less than 30 liters of Buffer B4 and is complete when a stable UV baseline is reached.

The rDSPA α1 is eluted from the column with not less than 30 liters of Buffer B5 and collected in a separate vessel. Elution is continued until a stable UV baseline is reached. The column is then cleaned for reuse (not to exceed 50 cycles of use). The Column B product (or eluate) is stored at 2°–8° C. for not more than 15 days before further processing. The average recovery was 91% and the average (protein) purity of the eluate was 97%.

3. Affinity chromatography (Column C). The Column B product is next chromatographed using Sephacryl S-400 (Pharmacia) (Column C). This step facilitates a buffer exchange to aid formulation and also helps in the inactivation/removal of viral contaminants. The Column C buffers consist of Buffer C1: Equilibration buffer (20 mM HCl, 19% EtOH), Buffer C2: Wash buffer (20 mM HCl), Buffer C3:Elution and Storage buffer (200 mM glycine, sterile filtered), and Buffer C4:Strip buffer (0.1N NaOH). The following column operating parameters are appropriate for a column volume of 10 liters. Not more than 20 grams of rDSPA α1 can be loaded on the column per run. The column is loaded at a flow rate of not more than 0.5 liters per minute and not more than 15 psi column pressure. The eluates from one or more Column B runs are pooled, then diluted with one part Buffer C2 and two parts Buffer 5 eluate. The final ethanol concentration will be approximately 19%.

Prior to loading, the column is equilibrated with not less than 15 liters of Buffer C1 until the effluent is pH 1.80 (±0.20). After loading the column is washed with not less than 30 liters of Buffer C2. The column is properly washed when the UV signal is stable. The product is eluted from the column with not less than 20 liters of Buffer C3 and collected in a separate vessel. Elution is continued until a stable UV baseline is reached.

After eluting the product, the column is stripped with not less than 12 liters of Buffer C4 and stored until reuse not to exceed 20 cycles. The Column C product (or eluate) is diluted to a concentration of ≤1 mg per milliliter with Buffer C3 and stored at 2°–8° C. for further processing. The average recovery of rDSPA α1 was 97% and the average (protein) purity of the eluate was 98%.

The concentration and formulation steps followed the completion of the purification steps above and was performed on the S-400 affinity column eluate, which had been stored for not more than 70 days. Column C eluates were pooled and concentrated by a spiral-wound ultrafiltration membrane that removes low molecular weight substances (30,000 dalton cut-off). The product was collected into a pyrogen free container at a concentration greater than 8 mg/mL. Mannitol was added to a 4% final concentration.

Final formulation buffer (200 mM glycine, 4% mannitol (w/v) was added to bring the concentration of the bulk formulated product to 7.5 mg/mL. The bulk formulated product is then sterile filtered, dispensed into vials and lyophilized.

While the present invention has been described with reference to the specific embodiments thereof, it should be understood by those skilled in the art that various changes may be made and equivalents may be substituted without departing from the true spirit and scope of the invention. In addition, many modifications may be made and equivalents

What is claimed is:

1. A method for purifying rDSPA α1 from a biological medium, the method comprising the following steps:
   (a) applying the medium to a cation exchange resin under loading conditions which result in selective binding of rDSPA α1 to the cation exchange resin;
   (b) optionally, washing the cation exchange resin to remove non-rDSPA α1 proteins and non-protein contaminants;
   (c) selectively eluting the bound rDSPA α1 from the cation exchange resin;
   (d) applying the rDSPA α1-containing eluent from step (c) to a hydrophobic interaction resin under loading conditions which result in selective binding of rDSPA α1 to the hydrophobic interaction resin;
   (e) optionally, washing the hydrophobic interaction resin to remove non-rDSPA α1 protein and non-protein contaminants;
   (f) selectively eluting the bound rDSPA α1 from the hydrophobic interaction resin;
   (g) applying the rDSPA α1-containing eluent from step (f) to an affinity chromatography resin under loading conditions which result in the selective binding of rDSPA α1 to the affinity chromatography resin;
   (h) optionally, washing the affinity chromatography resin to remove non-rDSPA α1 protein and non-protein contaminants;
   (i) selectively eluting the bound rDSPA α1 from the affinity chromatography resin to produce substantially pure rDSPA α1 in an aqueous solution.

2. The method of claim 1, wherein the biological medium is a conditioned medium.

3. The method of claim 1, wherein the cation exchange resin in step (a) is comprised of silica gel particles, cross-linked agarose, or cross-linked polymethacrylate polymers, derivatized with carboxyl or carboxyalkyl groups.

4. The method of claim 3, wherein the cation exchange resin is comprised of a matrix of silica particles covalently bound to polyethyleneimine silane, wherein the amino groups of the polyethyleneimine silane have been derivatized with carboxyl groups.

5. The method of claim 3, wherein the loading conditions in step (a) include applying the media at a pH between 4 and 7.

6. The method of claim 4, wherein the elution of rDSPA α1 in step (c) is performed using a buffer containing 50 mM NaPhos and between 100 mM and 500 mM NaCl, or a buffer of equivalent ionic strength.

7. The method of claim 1, wherein the hydrophobic interaction resin in step (d) is an uncharged resin, derivatized with alkyl chains of 1–10 carbons in length or with arylalkyl groups.

8. The method of claim 7, wherein the uncharged resin is comprised of silica gel particles, cross-linked agarose, or a cross-linked polymethacrylate polymer.

9. The method of claim 7, wherein the uncharged resin is comprised of semi-rigid spherical beads synthesized by a copolymerization of ethylene glycol and methacrylate type polymers, derivatized with butyl groups.

10. The method of claim 9, wherein the loading conditions in step (d) include applying the eluent from step (c) at a pH between 3 and 5.

11. The method of claim 9, wherein the loading conditions in step (d) include applying the eluent from step (c) in 50 mM NaPhos, 500 mM NaCl, pH adjusted to 4 with phosphoric acid, or in a buffer of equivalent ionic strength.

12. The method of claim 9, wherein the elution in step (f) is performed using a buffer containing 20 mM HCl and having an ethanol concentration greater than 25%.

13. The method of claim 12, wherein the ethanol concentration is between 28.5% and 30%.

14. The method of claim 12, wherein the ethanol concentration is 29%.

15. The method of claim 1, wherein the affinity chromatography resin of step (g) is comprised of a cross-linked co-polymer of allyl dextran and N,N'-methylene bisacrylamide in the form of beads with a diameter between 25 and 75 um.

16. The method of claim 15, wherein the beads are capable of fractionating globular proteins between 20,000 and 8,000,000 kDa.

17. The method of claim 15, wherein the loading conditions in step (g) include applying the eluent from step (f) at a pH between 1 and 4.

18. The method of claim 15, wherein the elution in step (i) is performed using a buffer containing 200 mM glycine at a pH between 3 and 6, or a buffer of equivalent ionic strength.

19. The method of claim 1, further comprising concentrating the aqueous solution of rDSPA α1.

20. The method of claim 19, further comprising lyophilizing the concentrated rDSPA α1 solution.

21. The method of claim 1, further comprising concentrating the aqueous solution of rDSPA α1 and lyophilizing the concentrated rDSPA α1 solution.

22. The method of claim 1, wherein the method comprises the following steps:
   (a) applying the medium at a pH between 4 and 7, to a cation exchange resin comprised of silica gel particles, cross-linked agarose, or cross-linked polymethacrylate polymers, derivatized with carboxyl or carboxyalkyl groups, which results in selective binding of rDSPA α1 to the cation exchange resin;
   (b) optionally, washing the cation exchange resin to remove non-rDSPA α1 proteins and non-protein contaminants;
   (c) selectively eluting the bound rDSPA α1 from the cation exchange resin using a buffer containing 50 mM sodium phosphate and between 100 mM and 500 mM NaCl, or a buffer of equivalent ionic strength;
   (d) applying the rDSPA α1-containing eluent from step (c) at a pH between 3 and 5 to a hydrophobic interaction resin comprised of silica gel particles, cross-linked agarose, or cross-linked polymethacrylate polymers, which results in selective binding of rDSPA α1 to the hydrophobic interaction resin;
   (e) washing the hydrophobic interaction resin to remove non rDSPA α1 protein and non-protein contaminants;
   (f) selectively eluting the bound rDSPA α1 from the hydrophobic interaction resin using a buffer containing 20 mM HCl and having an ethanol concentration greater than 25%;
   (g) applying the rDSPA α1-containing eluent from step (f) at a pH between 1 and 4 to an affinity chromatography resin comprised of a cross-linked polymer of allyl dextran and N,N'-methylene bisacrylamide in the form of beads with a diameter between 25 and 75 um, which results in the selective binding of rDSPA α1 to the affinity chromatography resin;

(h) optionally, washing the affinity chromatography resin to remove non-rDSPA α1 protein and non-protein contaminants;

(i) selectively eluting the bound rDSPA α1 from the affinity chromatography resin with a buffer containing 200 mM glycine at a pH between 3 and 6 or a buffer of equivalent ionic strength, to produce substantially pure rDSPA α1 in an aqueous solution.

23. A method for the isolation and purification of rDSPA α1 from a biological medium, the method comprising the following steps:

(a) applying the medium at a pH of 5 to a cation exchange resin comprised of a matrix of silica particles covalently bound to polyethyleneimine silane, wherein the amino groups have been derivatized with carboxyl groups, which results in selective binding of rDSPA α1 to the cation exchange resin;

(b) washing the cation exchange resin at pH 5 with 100 mM NaOAc and 50 mM $NaPO_4$ at pH 7.5, to remove non-rDSPA α1 protein and non-protein contaminants;

(c) eluting the bound rDSPA α1 from the cation exchange resin with a buffer containing 50 mM sodium phosphate and 500 mM sodium chloride at pH 7.5;

(d) applying the rDSPA α1-containing eluent from step (c) at pH 4 to a hydrophobic interaction resin comprised of semi-rigid spherical beads synthesized by a copolymerization of ethylene glycol and methacrylate type polymers derivatized with butyl groups, which results in selective binding of rDSPA α1 to the hydrophobic interaction resin;

(e) washing the hydrophobic interaction resin with 20 mM HCl and then with 20 mM HCl containing 19% EtOH to remove non-rDSPA α1 protein and non-protein contaminants;

(f) eluting the bound rDSPA α1 from the hydrophobic interaction resin with a buffer containing 29% ethanol and 20 mM hydrochloric acid at pH 2.5;

(g) applying the rDSPA α1-containing eluent from step (f) at pH 2.5 to an affinity chromatography resin comprised of a cross-linked polymer of allyl dextran and N,N'-methylene bisacrylamide which fractionates globular proteins between 20,000 and 8,000,000 kDa, which results in the selective binding of rDSPA α1 to the affinity chromatography resin;

(h) washing the affinity chromatography resin with 20 mM HCl to remove non-rDSPA α1 protein and non-protein contaminants;

(i) eluting the bound rDSPA α1 from the affinity chromatography resin with a buffer containing 200 mM glycine at a pH between 4 and 5, to produce substantially pure rDSPA α1 in an aqueous solution.

* * * * *